United States Patent [19]
Maxwell et al.

[11] 3,949,089

[45] Apr. 6, 1976

[54] SUBSTITUTED GUANIDINE COMPOUNDS AS ANTIFIBRILLATORY AGENTS

[75] Inventors: Robert Arthur Maxwell, Armonk, N.Y.; Eric Walton, Wrotham, England

[73] Assignee: Burroughs Wellcome Co., Research Triangle Park, N.C.

[22] Filed: Jan. 14, 1974

[21] Appl. No.: 433,413

Related U.S. Application Data

[62] Division of Ser. No. 48,490, June 22, 1970, abandoned.

[30] Foreign Application Priority Data

June 23, 1969 United Kingdom............... 31684/69

[52] U.S. Cl. ............................................. 424/326

[51] Int. Cl.² ........................................ A61K 31/155
[58] Field of Search .................................... 424/326

[56] References Cited
UNITED STATES PATENTS 3,168,562  2/1965  Walton et al. ..................... 424/326

*Primary Examiner*—Jerome D. Goldberg
*Attorney, Agent, or Firm*—Donald Brown

[57] ABSTRACT

Acid addition salts of N-p-methylbenzyl-N',N''-dimethylguanidine and of N-p-methoxybenzyl-N',N''-dimethylguanidine.

The compounds have antiarrhythmic properties, and are useful specifically as antifibrillatory agents.

17 Claims, No Drawings

SUBSTITUTED GUANIDINE COMPOUNDS AS ANTIFIBRILLATORY AGENTS

This is a division of application Ser. No. 48,490, filed on June 22, 1970, now abandoned.

This invention relates to compounds useful in the treatment of arrhythmia.

It has previously been proposed to employ the powerful hypotensive drug bethanidine (N-benzyl-N',N''-dimethylguanidine) sulphate, in the treatment of cardiac arrhythmia, see "Bethanidine: a New Antifibrillatory Agent" Arch. Int. Pharmacedyn, 1966, Vol. 163, pp. 422–426. The drug has potent antiarrhythmic properties but the hypotensive action attributable to sympathetic blockade causes an undesirable substantial lowering of blood pressure. Thus, it is essential, when the drug is used, for the patients to be in intensive-care units of hospitals.

It has now been found that certain N-benzyl-N',N''-dimethylguanidine acid addition salts, namely the N-p-methylbenzyl- and N-p-methoxybenzyl-N', N''-dimethylquanidine acid addition salts possess unexpected advantages over that drug in the treatment of arrhythmia. These compounds not only have antiarryhythmic properties comparable to bethanidine, but also significantly less sympathetic blocking action, thus making possible the treatment of heart disorders with little or no adverse effect on blood pressure.

Among the types of arrhythmias which the compounds of this invention are effective in suppressing are ventricular fibrillations and atrial fibrillations. It has been found that an effective amount of the compounds, which are most desirably pharmacologically and pharmaceutically acceptable salts according to ths invention, may be used to treat and suppress ventricular and atrial fibrillations in mammals, such as humans, dogs, cats and the like.

According in one aspect the present invention provides acid addition salts of N-p-methylbenzyl-N',N''-dimethylguanidine and of N-p-methoxybenzyl-N', N''-dimethylquanidine.

In another aspect the present invention provides a pharmaceutical composition comprising an acid addition salt of N-p-methylbenzyl-N',N''-dimethylguanidine or of N-p-methoxybenzyl-N',N''-dimethylguanidine, in association with a therapeutically acceptable carrier.

In a further aspect the present invention provides a method of treatment of arrhythmia which comprises the administration of an effective amount of an acid addition salt of N-p-methylbenzyl-N',N''-dimethylguanidine or of N-p-methoxybenzyl-N',N''-dimethylguanidine to the patient.

The activity of the acid addition salts of N-p-methylbenzyl-N', N''-dimethylguanidine and of N-p-methoxybenzyl-N',N''-dimethylguanidine resides in the cation, the nature of the anion only being important for administration requirements. Administration of the compounds will often be over a prolonged period and in such cases the anion must be pharmacologically acceptable, that is, non-toxic, "non-toxic" meaning having no harmful effect on the patient after prolonged treatment, and as used herein the term non-toxic has this meaning. Bromides and iodides have physiological activity inherent in their anions which may be undesirable especially upon prolonged administration. Salts which are especially preferred for therapeutic use are the chlorides, sulphates and sulphonates such as the p-toluenesulphonate. The salts of N-p-methoxybenzyl-N',N''-dimethylguanidine are particularly preferred from the point of view of their therapeutic activity.

The acid addition salts of N-p-methylbenzyl-N',N''-dimethylguanidine and of N-p-methoxybenzyl-N', N''-dimethylguanidine may be prepared by any of the known methods for preparing N-aralkyl-N', N''-dialkylguanidines.

For example, they may be prepared by the reaction of a guanidine and a compound capable of replacing a quanidine-hydrogen atom by a benzyl or methyl group, as required. This may be represented by the reaction diagram (a)

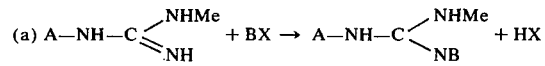

where one of A and B is the p-methylbenzyl or the p-methoxybenzyl group and the other is the methyl group, and X is a proton accepting group or atom such as a sulphonate group or a halogen atom. Such a reaction is usually carried out in a basic medium.

As another example, the salts of the invention may be produced by the reaction of an appropriate amine or a salt thereof with an S-substituted isothiourea or salt thereof, an O-substituted isourea or salt thereof, an isocyandihalide, an imidocarbonate or imidothiocaronate, a diimide, or a formamidine substituted by an unsaturated heterocyclic group containing at least two nitrogen atoms in the ring, one of which is attached to the carbon atom of the formamidine structure. These reactions may be illustrated by the following reaction diagrams:

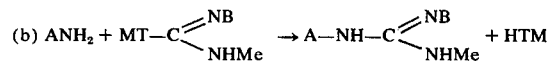

where one of A and B is the p-methylbenzyl or the p-methoxybenzyl group and the other is the methyl group, M is a reactive sustituent group in particular a hydrocarbon group, and T is an oxygen or a sulphur atom. M is preferably an alkyl group of one to four carbon atoms, especially methyl or ethyl, and B is preferably the p-methylbenzyl or the p-methoxybenzyl group; either the amino or the urea derivative is advantageously present as an acid addition salt such that during the reaction there is about one molecular equivalent of acid present.

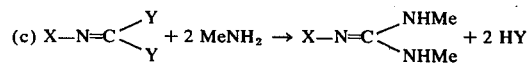

where X is the p-methylbenzyl or the p-methoxybenzyl group, and Y is a halogen atom or the group TM, where T and M are as defined above; preferably M is an alkyl group of one to four carbon atoms. When Y is a halogen atom it is preferably a chlorine or bromine atom; this reaction is conveniently carried out in an alcohol, especially preferred being an alcohol such as methanol or ethanol containing an inert solvent such as ether or benzene, and the methylamine is desirably used in excess. When Y is the group TM, then T is preferably oxygen and M preferably an alkyl group of one to six carbon atoms, especially ethyl or methyl; this reaction is normally carried out in an aqueous alcohol medium, whilst the preferred temperature range is from 10° to 30°C; and the methylamine is advantageously present as a mixture of the base and an acid addition salt thereof, the molecular proportion of the base exceeding that of the salt.

(d)

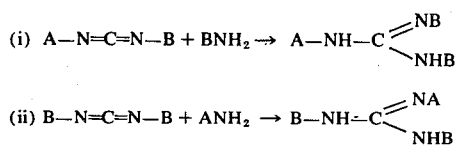

where A is the p-methylbenzyl or the p-methoxybenzyl group and B is the methyl group. These reactions may be carried out in alcoholic solution.

where one of A and B is the p-methylbenzyl or the p-methoxybenzyl group and the other is the methyl group, and Q is an optionally substituted unsaturated heterocyclic group containing at least two nitrogen atoms in the rings, one of which is attached to the carbon atom of the —C: (NMe)NHB structure. Examples of Q are pyrazolyl, dialkylpyrazolyl, alkyl-arylpyrazolyl, dialkylmonohalo-pyrazolyl, imidazolyl, triazolyl or tetrazolyl; 3,5-dimethylpyrazol — 1 — yl is preferred.

Salts of N-p-methylbenzyl-N',N''-dimethylguanidine and of N-p-methoxybenzyl-N',N''-dimethylguanidine may also be obtained from the appropriate base or other salts. For example, the sulphate may be prepared from the iodide or chloride by reaction with silver sulphate, or from the base by reaction with sulphuric acid. In an analogous manner salts may be converted to the N-p-methylbenzyl-N',N''-dimethylguanidine or the N-p-methoxybenzyl-N',N''-dimethylguanidine base by treatment with a convenient base, such as sodium hydroxide.

The present invention also provides the above methods of preparation of acid addition salts of N-p-methylbenzyl-N',N''-dimethylguanidine and of N-p-methoxybenzyl-N',N''-dimethylguanidine.

The compounds in the present invention may be presented in any acceptable pharmaceutical composition. Compositions for oral or practical administration are preferred. Oral administration is especially preferred.

For oral administration, fine powders or granules of the compounds may contain diluting, and/or surface active agents, and may be presented in a draft in water or in a syrup, in capsules or cachets in the dry state or in a non-aqueous suspension, when suspending agents may be included; in tablets, when binders and lubricants may be included; or in a suspension in water, a syrup, an oil or a water/oil emulsion. Where desirable or necessary flavouring, preserving, suspending, thickening or emulsifying agents can be included. Tablets and granules are preferred, and these may be coated.

For parenteral administration, the compounds may be presented in aqueous injection solutions which may contain antioxidants, buffers, bacteriostatic agents which solubilise a relatively insoluble compound, and solutes which render the salt isotonic with the blood in aqueous suspensions when suspending and thickening agent may also be included; or in non-aqueous solutions and suspensions if the particular compound selected is affected by water.

Dosages are preferably in the range 1 to 10 mg/kg of the base, especially about 4 mg/kg. Desirably the pharmaceutical compositions are presented in unit dosage form, usually containing in the range 100 to 600 mg. of base.

The following examples illustrate the invention.

EXAMPLE 1

A stirred solution of p-hydroxybenzonitrile (100 g.) in N-sodium hydroxide (1 liter) was treated at room temperature with dimethylsulphate drop by drop. After 24 hours the solid p-methoxybenzonitrile (93 g.) (m.p. 60°C – 64°C) was collected, washed with water, and dried on a porous plate. This product was dissolved in ethanol (500 ml) and hydrogenated at 100°C and 100 atmospheres in the presence of Raney nickel (5 g.). The filtrate was neutralised with 2N-HCl, evaporated and the residue crystallised from methanol-ether to give p-methoxybenzylamine hydrochloride, m.p. 210°C (softens) to 240°C (63 g.).

A solution of p-methoxybenzylamine (23 g.) in ether (150 ml.) was slowly treated with a solution of methyl isothiocyanate (12.4 g.) in ether (200 mls). The solution was allowed to cool and when cold the precipitated N-p-methoxybenzyl-N'-methylthiourea (23 g.) (m.p. 100° – 104°C) was collected.

A solution of the thiourea (18.5 g.) and methyl iodide (7 ml.) in methanol (75 ml.) was gently refluxed for 2 hours. The product was evaporated to dryness and the residual yellow oil was treated with ethanol-ether to give crystals of the isothiourea hydriodide (25 g.) m.p. 129° – 131°C.

A solution of the isothiourea hydriodide in 33% methanolic methylamine (20 ml.) plus a little water (3 – 5 ml.) was gently refluxed for 4½ hours. The product was evaporated to dryness and the resulting solid crystallised from methanol-ether to give the guanidine hydriodide, m.p. 161° – 164°C.

EXAMPLE 2

A well stirred solution of sodium hydroxide (240 g.), sodium cyanide (181 g.) and ethanol (480 ml.) in water (1800 ml.), was cooled in a carbon dioxide-ethanol bath and was freely treated with chlorine gas (double- or treble-tube delivery) at such a rate as to maintain the solution at −10°C to 0°C. After about half-an-hour, iminocarbonate (oil) and chloriminocarbonate (solid) began to separate. Stirring and addition of chlorine was continued until neutrality was approached (pH.8). A white crystalline-product was collected, ground up, well washed with water, and dried on a porous plate. Yield 200 – 220 g, m.p. 38° – 41°C.

This product (70 g.) was dusted into a solution of arsenious oxide (51 g.), potassium hydroxide (138 g.) in water (580 ml.) and the mixture was shaken vigorously for about 15 minutes. The temperature was maintained at 37° to 42°C by cooling. The resulting oily layer was extracted with ether. Evaporation of the sodium hydroxide-dried extract gave diethyl iminocarbonate (ca. 47 g.) (b.p. 42° – 44°C/15 mm.), which was used in the following stage without distillation.

p-methyoxybenzylamine hydrochloride (9.4 g.) in water (100 ml.) was treated with diethyliminocarbonate (5.6 g.). An oil, which separated on warming, was extracted with ether (9 g.).

This product (4.5 g.) and methylamine sulphate (1.48 g.) in water (2 ml.) were mixed wih 33% ethanolic methylamine (15 ml.) and the mixture was shaken to a homogeneous solution and then left 3 days at room temperature. The product was evaporated to dryness and the residual solid dissolved in water (10 ml.), treated with excess of 10N-sodium hydroxide solution and the resulting oily layer well extracted with ether. The extract, dried over solid sodium hydroxide, on evaporation gave the guanidine base as a syrup. From this, the sulphate was obtained by neutralisation with dilute sulphuric acid and evaporation. The sulphate was crystallised from methanol-ether to give a white solid, m.p. 273°C.

EXAMPLE 3

Diethyliminocarbonate was prepared in essentially the same manner as in Example 2 except that in the first stage the temperature was $-20°C$ and bromine was used instead of chlorine to give bromoiminocarbonate, and in the second stage sodium thiosulphate was used instead of arsenious oxide.

p-Methoxybenzylamine (95.4 g.) in water (360 ml.) was treated at less than 20°C with hydrochloric acid (58 mls of concentrated acid in 90 mls of water) so that the resultant mixture had a pH. of 4.7. A solution of diethyliminocarbonate (75.9 g) in toluene (540 ml.) was added and the whole stirred for 22 hours. The toluene layer was separated, washed with water and evaporated to give an oily residue of p-methoxybenzyl diethylimino-carbonate.

This product (145 g.) was added to a methylamine solution at 20°C obtained by mixing water (30 ml.) and sulphuric acid (27.2 g.) and adding them to methylamine (255 g.) of a 10 per cent aqueous solution. Industrial alcohol was added and the whole stirred overnight, the excess amine and solvent were evaporated off and the solid dissolved in water (about 300 ml.). Extraction with toluene, then water, followed by evaporation resulted in a solid which was dissolved in methanol (about 200 ml.) at 60°C. Acetone (320 ml.) was added and the precipitate collected, washed with ethanol and in vacuo at 80°C to give N-p-methoxybenzyl-N',N''-dimethylguanidine sulphate (m.p. 273° – 274°C).

EXAMPLE 4

A solution of N,N',S-trimethylisothiourea hydriodide, m.p. 208°–212° (9.84 g.) and p-methyl-benzylamine (4.84 g.) in ethanol (10 ml.) was refluxed for 3½ hours, filtered, and refluxed for a further 2½ hours. The solution was then concentrated, and the solid that separated was collected and crystallised from methanol-ethanol to give N-p-methylbenzyl-N', N''-dimethyl-guanidine hydriodide, m.p. 204° – 207°. Recrystallised from water, the m.p. rose to 209° – 212°.

EXAMPLE 5

A solution of p-methylbenzylamine hydrochloride (11 g.) in water (200 ml.) was treated with diethyl iminocarbonate (7.74 g.) in water (50 ml.) to give an oil, which was extracted with ether. Evaporation gave diethyl N-p-methylbenzyliminocarbonate (11 g.).

A mixture of this oil (11 g.), 30% ethanolic methylamine (50 ml.) and a solution of methylamine sulphate (4 g.) in water (20 ml.) was shaken to give a clear solution. After 3 days at room temperature it was evaporated to a white solid, which with strong sodium hydroxide, gave N-p-methyl-benzyl-N,N'-dimethylguanidine, m.p. 118° – 125°, after extraction with ether, and evaporation. The hydriodide, from methanol-ether, melted at 212° – 214°.

EXAMPLE 6

Tablets (0.55 g.) of N-p-methylbenzyl-N',N''-dimethylguanidine hydriodide were made by mixing the salt (0.25 g.) in a fine powder with lactose (0.25 g.) and starch (0.05 g.), granulating the mixture with alcohol or alcoholic polyvinyl pyrrolidone or a mixture of equal parts of alcohol and water, drying the granules at 40°, adding magnesium stearate (0.010 g.) as a lubricant and compressing the mixture.

EXAMPLE 7

Tablets (0.208 g.) of N-p-methylbenzyl-N', N''-dimethylguanidine hydriodide were made by granulating the salt (0.1 g.) in a fine powder and lactose (0.1 g.) with gelatin (0.005 g.) in equal parts of alcohol and water. Magnesium stearate (0.003 g.) as a lubricant was added, and the mixture compressed directly.

EXAMPLE 8

Injection solutions containing N-p-methylbenzyl-N',-N''-dimethylguanidine hydriodide in water for Injection (0.2 g. per ml.) were made by autoclaving the solution at 15 lb. steam pressure for 30 minutes in until dose ampoules of multidose containers. For the latter, the Water for Injection contained benzyl alcohol (1.0%), phenol (0.5%) or chlorocresol (0.1%).

EXAMPLE 9

Tablets and injection solutions similar to those in Examples 6 to 8 were prepared using N-p-methoxybenzyl-N',N''-dimethylguanidine sulphate for the p-methyl compound.

We claim:

1. A method of treatment of arrhythmia in a mammal suffering from arrhythmia which comprises administering to said mammal an effective arrhythmia treatment amount of a pharmaceutically acceptable acid addition salt of N-p-methoxybenzyl-N',N''-dimethylguanidine.

2. A method according to claim 1 wherein the arrhythmia which is treated is atrial fibrillation.

3. A method according to claim 2 wherein the mammal is a human.

4. A method according to claim 1 in which the acid addition salt is the sulphate salt of N-p-methoxybenzyl-N',N''-dimethylguanidine.

5. A method according to claim 1 wherein the effective amount is 1 to 10 mg of the base /kg of mammal bodyweight.

6. A method according to claim 5 wherein the arrhythmia which is treated is ventricular or atrial fibrillation.

7. A method of suppressing ventricular or atrial fibrillations in a mammal having a heart disorder which comprises administering to said mammal an effective ventricular or atrial fibrillation suppression amount of a pharmaceutically acceptable acid addition salt of N-p-methoxybenzyl-N',N''-dimethylguanidine.

8. A method according to claim 7 in which the fibrillation and the amount is an effective ventricular fibrillation suppression amount.

9. A method according to claim 8 in which the acid addition salt is the sulphate salt of N-p-methoxybenzyl-N',N''-dimethylguanidine.

10. A method according to claim 8 in which said effective amount is 1 to 10 mg. of the base /kg. of mammal bodyweight.

11. A method according to claim 7 in which an effective amount is 1 to 10 mg of the base /kg of mammal bodyweight.

12. A pharmaceutical composition in solid form for administration to treat or suppress arrhythmia, comprising per dosage unit an effective arrhythmia treatment or suppression amount of a pharmaceutically acceptable acid addition salt of N-p-methoxybenzyl-N',N''-dimethylguanidine and a therapeutically acceptable carrier therefor.

13. A composition according to claim 12 in which the arrhythmia is ventricular or atrial fibrillation and the effective amount is a ventricular or atrial fibrillation amount.

14. A composition according to claim 13 in which the salt is the sulphate salt of N-p-methoxybenzyl-N',N''-dimethylguanidine.

15. A pharmaceutical composition according to claim 12 in a form for oral administration.

16. A pharmaceutical composition according to claim 15 in the form of a tablet or capsule.

17. A pharmaceutical composition according to claim 15 in the form of a discrete dosage unit containing 100 to 600 mg of the base.

* * * * *